United States Patent [19]

Shenk et al.

[11] Patent Number: 4,866,644

[45] Date of Patent: Sep. 12, 1989

[54] OPTICAL INSTRUMENT CALIBRATION SYSTEM

[76] Inventors: John S. Shenk, Rd #1, 109 Sellers Lane, Port Matilda, PA 16870; Mark O. Westerhaus, 1442 Westerly Pkwy., State College, Pa. 16801

[21] Appl. No.: 901,875

[22] Filed: Aug. 29, 1986

[51] Int. Cl.$^4$ .................. G01N 37/00; G01N 21/01
[52] U.S. Cl. ................. 364/571.02; 73/1 R; 364/525; 356/124
[58] Field of Search .......... 364/509, 556, 496, 497, 364/525, 571, 512, 578, 553, 581; 73/23.1, 1 R; 250/222.1, 571; 358/107; 356/124, 127, 26

[56] References Cited

U.S. PATENT DOCUMENTS

| | | | |
|---|---|---|---|
| 3,526,761 | 9/1970 | Smith | 364/553 |
| 3,861,788 | 1/1975 | Webster | 350/315 |
| 3,973,112 | 8/1976 | Sloane | 364/553 |
| 4,084,248 | 4/1978 | Scott | 364/525 X |
| 4,199,816 | 4/1980 | Humphrey | 364/571 |
| 4,200,934 | 4/1980 | Hofmann | 364/525 X |
| 4,328,552 | 5/1982 | Stovall | 364/553 X |
| 4,357,668 | 11/1982 | Schwartz et al. | 364/497 |
| 4,358,822 | 11/1982 | Sánchez | 364/178 X |
| 4,365,304 | 12/1982 | Ruhman et al. | 364/553 X |
| 4,394,744 | 7/1983 | Wrench, Jr. | 364/553 |
| 4,481,596 | 11/1984 | Townzen | 364/571 |
| 4,509,132 | 4/1985 | Kavaya | 364/578 X |
| 4,578,762 | 3/1986 | Wong | 364/571 X |
| 4,692,299 | 9/1987 | Crew et al. | 364/553 X |
| 4,692,883 | 9/1987 | Nelson et al. | 364/525 X |
| 4,697,236 | 9/1987 | Butts et al. | 364/525 X |
| 4,744,657 | 5/1988 | Aralis et al. | 364/571 |
| 4,779,216 | 10/1988 | Collins | 364/525 |

Primary Examiner—Parshotam S. Lall
Assistant Examiner—Joseph L. Dixon
Attorney, Agent, or Firm—Lane and Aitken

[57] ABSTRACT

In a calibration system for optical instruments of the type which make measurements at incrementally spaced wavelengths throughout a spectrum, a plurality of standard samples are measured by a master instrument and a field instrument. The measurement data obtained from each instrument are then statistically correlated to determine a calibration file which is stored with the field instrument. The calibration file includes identification on the field instrument of index locations at which the field instrument will respond to the same wavelength as corresponding index points on the master and includes correction coefficients for each of the index locations. The calibration file is stored in a computer connected to the field instrument and the computer is provided with a program to correct the measurements made by the field instrument in accordance with the stored calibration file.

11 Claims, 2 Drawing Sheets

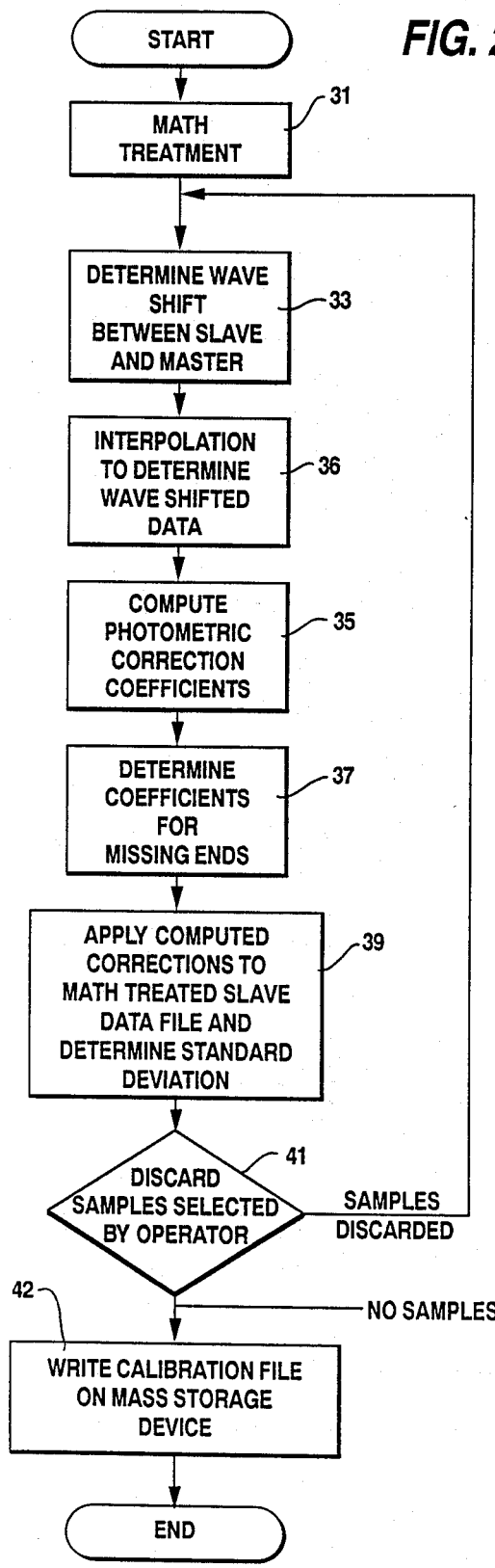
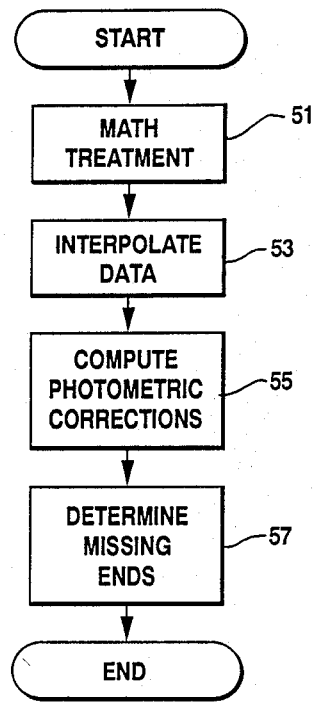

OPTICAL INSTRUMENT CALIBRATION SYSTEM

BACKGROUND OF THE INVENTION

This invention relates to a method of calibrating optical instruments and to a system of optical instruments which are calibrated in accordance with the method of the invention.

Several different kinds of optical instruments which analyze test samples by the reflectance or transmissivity of the samples at narrow bandwidths distributed throughout a spectrum are currently in use. These instruments are used to make quantitative measurements on agricultural samples, such as grain, meat, or hay and also are used to make measurements of the color of samples such as in the case of paint samples.

In one instrument of the prior art, light is dispersed into a spectrum by means of a grating which is oscillated at a relatively high rate of speed. Examples of this type of instrument are disclosed in U.S. Pat. Nos. of Landa 4,285,596 and 4,264,205. In another type of instrument, a plurality of interference filters are mounted on a filter wheel and each filter is rotated by the filter wheel sequentially into a path of collimated light. As the filter moves through a beam of collimated light, the angle of the filter to the incident light varies and the narrow bandwidth of light transmitted by the filter is changed. Examples of this latter type of instrument, which is called a tilting filter instrument, are disclosed in U.S. Pat. Nos. 3,861,788 to Donald R. Webster and 4,082,464 to Robert L. Johnson, Jr. In each of the above mentioned instruments, the narrow bandwidth of light transmitted by the instrument depends upon the angular position of an oscillating or rotating element. In the instrument with the oscillating grating, the transmitted bandwidth depends upon the angular position of the oscillating grating and outputs are obtained from the grating throughout a spectrum at two nanometer increments of the transmitted wavelength. In the tilting filter instrument, outputs are obtained at similarly small increments of the transmitted wavelengths.

SUMMARY OF THE INVENTION

Because manufacturing techniques are not perfect, each optical instrument of a given model, while intended to be like all other instruments of the same model, are not precisely the same, and accordingly will produce a different response from a given sample than other instruments of the same model. The present invention provides a technique of providing for each instrument in the field a file of calibration factors, which operate on the output data from the instrument so that each instrument will produce an output from a given test sample which is virtually the same for all instruments and in particular, is virtually the same as from a master instrument of the same model.

It was determined that the differences in the response from the different instruments occur primarily from the fact that the angular positions of the oscillating or rotating elements are not precisely the same relative to the index points for the instruments and also because the photometrics of the two instruments are different; that is the amplitude of an output signal received from the instrument for a given input wavelength amplitude will not be the same. To determine the calibration factors, a series of standard samples are selected. The standard samples are selected to have different response characteristics throughout the spectrum of the instrument and are selected from the type of samples of which the instrument is designed to measure. For example, if the instrument is to measure agricultural products such as grain, forage, soybeans etc., then samples of each of the agricultural products will be employed as the standard samples. One of the instruments of a given model is selected as the master instrument and the response of the master instrument at each index point of the instrument throughout the spectrum is measured and stored for each of the standard samples to provide a file of data for the master instrument. The standard samples are then measured on a field instrument to be calibrated to provide a corresponding file of data from the standard samples for the field instrument. Using statistical correlation techniques on the two files of data, the waveshift of each index point on the field instrument relative to the corresponding index points on the master instrument is determined and index locations on the field instrument which correspond precisely to the index points are stored in a computer file for the field instrument. Photometric corrections are also determined by statistical correlation and are stored in the computer file for the field instrument. When an unknown test sample is measured with the field instrument, the stored corrections are employed to provide an output from the field instrument which will be substantially the same output that would be obtained if that unknown test sample were measured with the master instrument.

Similar correlation techniques may be employed to make the output data from one type of instrument look substantially like the output data from another type of instrument. For example, the output data from the oscillating grating type instrument can be made to correspond to an instrument of the tilting filter type.

Accordingly, an object of the present invention is to provide an improved system for calibrating optical instruments.

Another object of the present invention is to calibrate field instruments, so that their outputs will correspond to a master instrument.

A further object of the invention is to provide a system of calibrated optical instruments in which field instruments in the field are calibrated to correspond with a master instrument.

Further objects and advantages of the present invention will become readily apparent as the following detailed description of the invention unfolds when taken into conjunction with the drawings.

BRIEF DESCRIPTION OF THE DRAWINGS

FIG. 2 is a flowchart of a program to compute a file of calibration factors which are employed in an optical instrument as shown in FIG. 1.

FIG. 3 is a flowchart of a program employed in an optical instrument as shown in FIG. 1 to make use of the calibration factors computed by the program illustrated in FIG. 2.

DESCRIPTION OF THE SPECIFIC EMBODIMENTS

Figure 1:
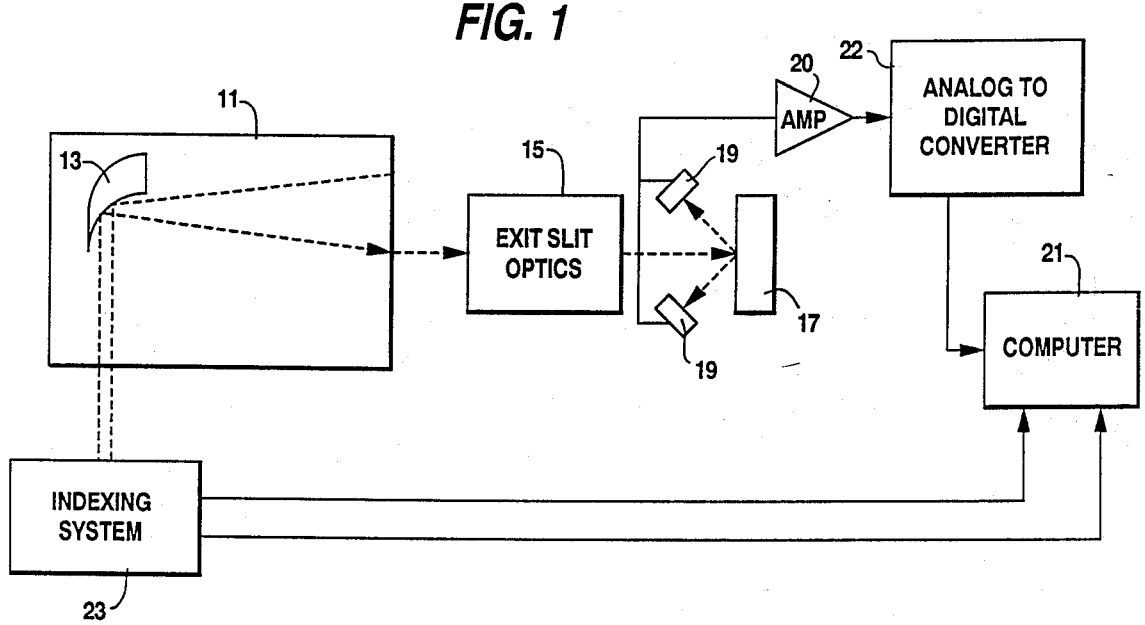
FIG. 1 schematically illustrates an optical instrument of the type in which the calibration system of the present invention is employed.

FIG. 1 schematically illustrates an optical instrument of a type for analyzing agricultural products such as manufactured by the Gardner/Neotec Division of Pacific Scientific Company, identified by the Gardner/Neotec Model No. 6250. Details of this instrument are disclosed in U.S. Pat. No. 4,264,205. As shown in FIG. 1, the instrument comprises a spectrometer 11 containing an oscillating grating 13. The grating 13 is irradiated with near-infrared light and disperses the light into a spectrum. An exit slit in the spectrometer is positioned to transmit a narrow bandwidth of the spectrum dispersed by the grating 13. As the grating oscillates, the bandwidth of the light passing through the exit slit is scanned through a range of the spectrum dispersed by the grating 13. The light passing through the exit slit is transmitted by exit slit optics 15 to irradiate a sample 17. Light reflected by the sample is detected by photodetectors 19, the output signals of which are combined and applied to an amplifier 20. The amplifier applies an amplified version of the combined photodetector signal to an analog to digital convertor 22, which converts successive samples of the output signal of the amplifier 20 to digital values. The digital output values from the analog to digital converter 22 are received by a computer 21. An indexing system 23 generates pulses as the grating oscillates and applies these pulses to the computer 21, which from the applied pulses keeps track of the angular position of the grating 13. The pulses produced by the indexing system 13 define incremental index points at which values of the output signal of the amplifier 20 are converted to digital values and stored in the computer 21. In the model 6250 instrument shown in FIG. 1, the index points are at two nanometer intervals of the spectrum dispersed by the grating 13. As a result, each time the grating 13 pivots through an angle to cause a two nanometer change in the wavelength of light passing through the exit slit of the spectrometer 11, a new digital value is obtained by the computer 21 corresponding to the reflectance of the sample at that wavelength. In this manner, the instrument obtains a file of data representing the reflectivity of the sample being measured throughout the operating range of the instrument.

If a given test sample were measured in two instruments, which are supposed to be the same, such as two instruments of Model No. 6250, the file of spectral data obtained by each instrument would not be exactly the same. The file of spectral data will vary from instrument to instrument, because the wavelength of light transmitted through the exit slit of the instrument will not be exactly the same at corresponding index points because of mechanical variances. Also the digitized light measurement at a given wavelength will not be exactly the same from instrument to instrument because of optical and electronic variances.

In accordance with the invention, one of the instruments, such as that shown in FIG. 1, is selected to be the master instrument. Other instruments of the same model, to be used in the field, are designated field instruments. A file of data called a calibration file is computed for each field instrument and stored in the computer 21 of such said field instrument. The calibration file is employed by the field instrument to correct the data representing the spectrum from any given test sample being analyzed by the field instrument to be substantially identical to the data that would be obtained from the given test sample by the master instrument. In this manner, the spectral response from each field instrument from any given test sample is made substantially the same as the master instrument and therefore, the corrected spectral response from each field instrument will be substantially the same.

To determine the calibration file for each instrument, a plurality of standard samples of the agricultural products of the type which the instrument is designed to measure are obtained. The number of samples employed may be varied but there should be enough to characterize the instrument and support the statistical correlation techniques employed in the invention. Accordingly, no fewer than five standard samples should be employed. In a typical example 30 standard samples may be employed. These samples, which for example may be grain, soybeans, meat, hay, etc., are selected to have varying optical responses throughout the operating spectral range of the instrument. The standard samples are measured by the master instrument to obtain for each of the standard samples a raw spectral set of data comprising the reflectance measurements obtained by the instrument at each index point of the instrument. The spectral sets as a group obtained by the master instrument are referred to as the master data file. The samples are then measured by a slave instrument to be calibrated to obtain corresponding slave data file comprising raw spectral sets of data, one from each sample.

The master data file and the corresponding field data file are inputted to a computer, which is programmed to compute a calibration file of data for the field instrument. The master data file and the field data file will each correspond to the reflectivity of each standard sample over the operating spectrum of the instrument. The values in each spectral set are sequential samples of a curve corresponding to the variation in the reflectivity of the corresponding sample throughout the operating spectrum of the instrument. If there are N standard samples there will be N values obtained by the master at each index point of the master and there will be N values obtained by the field instrument at each index point of the field instrument. For convenience, the set of values for a common index point in the spectrum shall be referred to as a correlation set.

A listing in source code of the computer programs to compute the file of calibration data for a field instrument of the type shown in FIG. 1 is listed in appendix A of this application which may be found in the patented file and the program is represented by the flowchart shown in FIG. 2. As shown in FIG. 2, the program first enters instruction sequence 31 in which any math treatment selected by the operator may be performed on the spectral sets. In the math treatment process, computer program performs operations corresponding to smoothing and differentiation. In the smoothing operation, each point in a spectral set is averaged with adjacent points to smooth out the curve represented by the spectral sets. In the operation corresponding to differentiation, each point is subtracted from the next adjacent point. The resulting differences will represent the differential of the curve represented by the original spectral set. The difference operation may be performed more than one time to obtain data corresponding to the second or higher order derivatives. The remainder of the program to compute the calibration file operates in the same whether it is on the raw spectral sets or on the smoothed and or differentiated data. As a result of the math treatment a processed spectral set of data will be obtained for each sample.

After the math treatment, the program enters instruction sequence 33 in which the waveshift between the master and the field instrument is determined for each index point on the master. To carry out this process, the correlation coefficient is determined between the correlation set for each index point on the master and the correlation set for each of several index points on the field instrument which are closest to such index point on the master. For example, each index point on the master may be correlated with five index points on the field instrument. The number of points employed in this correlation process is selectable by the operator and should be at least five. As a result of this correlation process, several correlation coefficients will be computed for each index point on the master. A set of correlation coefficients obtained in this manner for a given index point on the master shall be referred to as a window set.

The highest one of the correlation coefficients in a window set should be the closest index point on the field instrument corresponding to the index point on the master, but the identification of this index point on the field instrument does not provide a measurement of the waveshift between the two instruments with sufficient accuracy. To determine the precise waveshift, the correlation coefficient values are assumed to represent points on a quadratic equation model, $y = a + bx + cx^2$. The coefficients for this equation are determined by the least squares method and the maximum point of the curve represented by the resulting equation is determined. Since the index points from which the window set were calculated represent incrementally spaced angular positions of the oscillating grating of the field instrument, the maximum point of the curve of the quadratic equation will represent an angular position of the grating in the field instrument at which the field instrument will transmit the same wavelength that the master instrument transmits at the index point for which the calculation was made. Moreover, in the field instrument and in the master instrument, each index point is named by a nominal wavelength which the instrument is supposed to transmit and as pointed out above the wavelength changes in two nanometer increments for each index point on the field or master instrument. Accordingly, the difference between the maximum point of the quadratic equation and the position of the corresponding index point on the master will be directly related to the wave shift in the field instrument for the corresponding index point in the master. For example, if the maximum of the quadratic equation is determined to be 1.6 index points shifted from the corresponding index point in the master, the wave shift would be equal to $1.6 \times 2 = 3.2$ nanometers. If the quadratic equation has more than one maximum or if the maximum determined is more than one index point away from the index point at which the maximum correlation coefficient in the window set occurs, then the computed waveshift is disregarded in the subsequent calculations.

After a waveshift has been computed in this manner for each index point on the master, the resulting waveshifts are used to determine the coefficients by the least squares method in the equation model, $\lambda_s = A + B\lambda_m$. In this equation in $\lambda_m$ represents the nominal wavelength transmitted by the master at a given index point, and $\lambda_s$ represents an index location on the field instrument at which the field instrument will transmit the same wavelength as the master at the given index point. As pointed out above, each index point on the field instrument and on the master is named by the nominal wavelength which the instrument is designed to transmit at that wavelength. Thus the index points on the field or master instrument define a scale in wavelengths. Accordingly, the value of $\lambda_s$ is in wavelength units and represents an index position on the field instrument in terms of the nominal wavelength values by which each index point on the field instrument is named. The coefficients A and B are parameters to be estimated. Using values of $\lambda_s$ computed for each index point on the master, the coefficients A and B in the model are determined by least squares regression. Then from the equation, a set of shifted index locations are computed for the field instrument to correspond to the index points of the master. Most of the shifted index locations of the field instrument would normally be expected not to coincide with index points of the field instrument, but occur between index points on the field instrument. For example, the value of $\lambda_m$ for an index point on the master might be 1760 nanometers and the corresponding value of $\lambda_s$ computed from the equation might be 1762.4 nanometers. The value of $\lambda_s$ would then represent an index location on the field instrument between the index points on the field instrument nominally named 1762 nanometers and 1764 nanometers and be displaced from the 1762 nanometer index point by 0.2 parts of the increment between the two index points.

After computing the waveshift in the field instrument in instruction sequence 33, the program proceeds to instruction sequence 36, in which the program processes each spectral set into a wave shifted spectral set of data values with the values of each new spectral set corresponding to the index locations $\lambda_s$ determined in instruction sequence 33. This computation is carried out by interpolation. For example, if a spectral set value obtained for the index point nominally named 1762 nanometers is 0.553 and the spectral set value obtained for the index point nominally named 1764 nanometers is 0.563 and one of the values of $\lambda_s$ is 1762.4 nanometers so that it represents a point displaced from the 1762 nanometer index point by 0.2 parts of the segment between the 1762 nanometer and the 1764 nanometer index points, then the new spectral set value for $\lambda_s$ is determined from the equation $0.533 + (0.563 - 0.553) \times 0.2 = 0.555$. For each spectral set, a wave shifted spectral set of values is computed for each value of $\lambda_s$ in this manner. Accordingly, a wave shifted correlation set of values will be obtained for each value of $\lambda_s$ for which data are available.

From the wave shifted set of data thus determined, the photometric corrections are computed in instruction sequence 35. These are computed by assuming that the output from the master is related to the output from the field instrument by the model $L = D + EL'$, wherein L is a spectral response value obtained from the master at a given index point and L' is the corresponding wave shifted spectral response value obtained from the field instrument at the index location corresponding to the given index point on the master, and D and E are coefficients to be estimated by least squares regression. The values to be plugged in to the least squares regression calculation for a given spectral point on the master are the wave shifted correlation set of values determined for the corresponding value of $\lambda_s$ by the interpolation instruction sequence 36 described above. In this manner, values of D and E are determined for each pair of index point $\lambda_m$ and corresponding index location $\lambda_s$ on the master and field instrument respectively and from the coefficients thus determined, a corrected photometric value $L''$ may be determined for each value of $L'$ of wave shifted data according to the equation $L''=D+EL'$, in which D and E are the coefficients determined in instruction sequence 35 for the index location $\lambda_s$ corresponding to the value of $L''$. If the calibration were perfect, each value of $L''$ would precisely equal the corresponding value of L representing the photometric response of the master at the corresponding index point.

For some values of $\lambda_s$, called missing ends, there will be no correlation sets for which to compute the photometric correction values D and E. This missing data can result from the smoothing and or differentiation in the math processing instruction sequence 33 or from the wave shifting operations. In instruction sequence 37, the program computes this missing data by multiple regression, using the following equation model: $y_m=b_0+b_1S_1+b_2S_2+S_3$. In this equation $S_1=P_{n1}-S_3$, $S_2=P_{n2}-S_3$, and $S_3=(P_{n3}+P_{n4})/2$. $P_{n1}$ is a corrected photometric value $L''$ on the field instrument for which there is data nearest to the missing end being computed. $P_{n2}$ is a value of $L''$ at next nearest location after $P_{n1}$ for which there is data, $P_{n3}$ is a value of $L''$ at next nearest location after $P_{n2}$ for which there is data, and $P_{n4}$ is a value of $L''$ at the next nearest location after $P_{n3}$ for which there is data on the field instrument. In the multiple regression process to compute the coefficients, $b_0$, $b_1$, and $b_2$, the photometric output from the master obtained from each of the standard samples at the index point on the master corresponding to a missing end is used to provide the value $y_m$. The coefficients $b_0$, $b_1$, and $b_2$ thus computed can be used to compute the photometric output from the slave at the missing end on the slave using the formula $y_s=b_0+b_1S_1+b_2S_2+S_3$, in which $y_s$ will be the computed output on the field instrument for each missing end point for each standard sample.

As described above, a calibration file of correction values is computed for the field instrument. These correction values include the index locations, $\lambda_s$, on the field instrument which correspond to the index points on the master, that is the index locations on the field instrument where the field instrument will transmit substantially the same wavelength as the master. For each of these index locations thus determined, there will be two coefficients, D and E for the model equation $L''=D+EL'$. Also, as indicated above, a set of coefficients $b_0$, $b_1$, and $b_2$ are determined for each missing end point on the field instrument for the missing end equation $y_s=b_0+b_1S_1+b_2S_2+S_3$.

After completion of instruction sequence 37, the program enters into instruction sequence 39, in which the program applies the photometric coefficients to the wave shifted spectral sets obtained from each of the standard samples and determined in interpolation instruction sequence 36. To perform this operation, each wave shifted photometric value $L'$ determined in interpolation instruction sequence 36 is plugged into the equation $L''=D+EL'$ to determine the corrected value of $L''$ as described above. In addition, the values of $L''$ are plugged into the equation $y_s=b_0+b_1S_1+b_2S_2+S_3$ to determine for each spectral set a value of $y_s$ for each missing end point. In this manner, a complete corrected spectral set containing a value of each index location $\lambda_s$ will be determined for each of the standard samples.

The resulting corrected spectral sets are then compared for value with the corresponding spectral sets obtained from the master and the standard deviation for each spectral set is computed and displayed to the operator.

Following this operation, in decision sequence 41, the operator is given the option of discarding the data from those standard samples for which the standard deviation is too large. If the operator decides to discard some of the standard samples, the program returns to instruction sequence 33 and the process of computing the set of correction values and coefficients is repeated but with the spectral sets from the standard samples which were discarded in decision sequence 41 eliminated from the master and slave data files. When in decision sequence 41 it is determined that no samples are to be discarded, the process of computing the calibration file is completed.

The calibration file, comprising the index locations $\lambda_s$, the photometric coefficients D and E for each index location $\lambda_s$, and values of $b_0$, $b_1$, and $b_2$ for each missing end point is then stored on the mass storage device of the computer in instruction sequence 42. It will be apparent that instead of storing the values of the index locations $\lambda_s$ in the calibration file, the values of the coefficients A and B determined in the instruction sequence 33 could be stored since the values of $\lambda_s$ are determined directly from the values of these coefficients in accordance with the equation $\lambda_s=A+B\lambda_m$. The computed calibration file is then provided in the field instrument. In the preferred embodiment the master instrument stores the calibration file on a removable mass storage device, such as a floppy disc, and this storage device is installed in the field instrument. When the field instrument reads out photometric data from an unknown sample, the data are corrected in accordance with the data in the stored calibration file, so that the output from the field instrument obtained from the unknown sample will be substantially identical to that which would have been obtained from the master instrument, had the unknown sample been tested in the master instrument. In this manner, each instrument in the system of instruments is made to have an essentially identical response to that of the master and therefore, to each other.

FIG. 3 illustrates a flow chart for the program used by the field instrument to correct the photometric data obtained from an unknown sample by means of the stored calibration file. As shown in this figure, the program performs any selected math treatment, such as smoothing or differences on the photometric data in instruction sequence 51. The resulting processed data is then interpolated in accordance with the index location values $\lambda_s$ in the calibration file to determine a set of wave shifted photometric values $L_u'$ corresponding to the index location $\lambda_s$ respectively. The wave shifted data are then operated on in instruction sequence 55 by the correction coefficients D and E in accordance with the equation $L_u''=D+EL_u'$ to determine a set of corrected values $L_u''$ corresponding to the index locations $\lambda_s$. Then in instruction sequence 57, values $y_u$ are determined for the missing end points in instruction sequence 57 by the equation $y_u=b_0+b_1S_1+b_2S_2+S_3$. The values $b_0$, $b_1$, and $b_2$ are the values in the calibration file and the values of $S_1$, $S_2$, and $S_3$ are determined from the nearest values of $L_u''$ in the same manner that they were determined from the values of $L''$ in computing the coefficients $b_0$, $b_1$, and $b_2$. In this manner, a spectral set of values $L_u''$, and $y_u$ for the missing end points will be obtained from the unknown sample, which should be substantially identical to the photometric values that would be obtained from the unknown sample by the master instrument. The determined set of spectral values can then be displayed to the operator of the field instrument or made use of by the field instrument in analysis operations.

Figure 4:
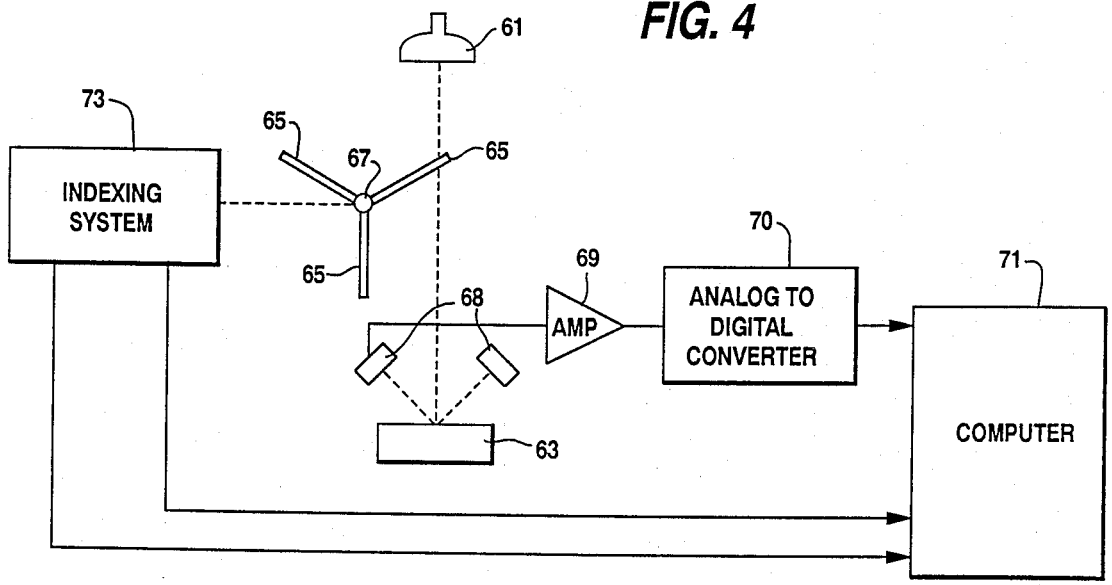
FIG. 4 is a schematic illustration of another optical instrument in which the calibration system of the present invention is employed.

In accordance with the invention, similar calibration files can be computed for instruments of the tilting filter type, such as the model 4250 manufactured by the Gardner/Neotec Division of Pacific Scientific Company. The model 4250 is schematically illustrated in FIG. 4. As shown in FIG. 4, a source of light 61 in the near infrared range is arranged to irradiate a sample 63. A set of interference filters 65 are mounted on an axle 67 in a paddle wheel arrangement to be continuously rotated in sequence into the beam of light passing from the source 61 to the sample 63. As the filters move through the light beam, they vary the wavelength transmitted to the sample. The filters are selected so that they scan a different part of the spectrum as they rotate through the light beam. To insure that the entire operative range of the instrument is covered, there will be some overlap between the scans of each of the filters. The light reflected by the sample 63 is detected by photodetectors 68, the output signals of which are combined and applied to an amplifier 69. The amplifier 69 amplifies the combined output signal of the photodetectors 68 and applies it to an analog to digital converter 70, which converts successive samples of the output signal of amplifier 69 to digital values. The digital values from the analog to digital converter are received by a computer 71. An indexing system 73 generates index pulses as the axle 67 rotates the filters 65 through the light beam and these index pulses are applied to the computer 71. By means of the index pulses produced by the indexing system 73, the computer 71 keeps track of the angular position of the axle 67 and the nominal wavelengths at which the instrument is supposed to transmit near infrared light to the sample 63 at any given instant of time.

The program for the computer to determine the calibration file for a model 4250 slave instrument as shown in FIG. 4, is essentially the same as the program for the model 6250 instrument except that in instruction sequence 33, the equation model for computing the wave shift is based on the equation $\sin^2\theta' = A + B\sin^2\theta$ wherein $\theta'$ is the tilt angle of the filter in the field instrument and $\theta$ is the tilt angle of the filter in the master. The tilt angle $\theta$ of a filter is related to the transmitted wavelength $\lambda$ by the equation $\sin^2\theta = R^2(1 - \lambda^2/C^2)$ in which R is the refractive index of the filter and C is the center wavelength of the filter. The coefficients A and B are parameters to be estimated by the least squares regression.

Appendix B which may be found in the patented file is the source code in Fortran of the program for computing the calibration file for the model 4250 instrument as schematically illustrated in FIG. 4.

In a similar manner, the invention may be applied to other types of instruments, such as the model 7000 instrument, also manufactured by the Gardner/Neotec Division of Pacific Scientific Company. The model 7000 instrument is also a tilting filter instrument which rotates filters sequentially through the light beam. However, in this instrument, the filters are mounted in a drum configuration rather than the paddle wheel configuration illustrated in FIG. 3.

Alternatively, in a similar manner, an instrument of one type may be designated as a field instrument and an instrument of another type may be designated as the master and the output from the instrument designated as a field instrument may be made to be substantially identical to the master of the different type. For example, a mode 6250 can be provided with a calibration file so as to make its output be essentially identical to the output obtained from the model 4250 instrument. The model 4250 data cannot be effectively calibrated to look like data from a model 6250 instrument because the model 4250 instrument does not cover enough of the spectral region covered by the model 6250 and the model 4250 data has too large a band pass. Model 6250 data can be made to look like model 4250 data because the larger band pass of the model 4250 can be simulated by smoothing the data from the model 6250. However, there would be no demand for a system in which model 6250 instruments are conformed to a master 4250 instrument because of the limitations in the spectral coverage and band pass in the model 4250 instrument. However, a model 6250 instrument can be used to advantage as a master for a model 4250 field instrument. In such a system, the model 6250 is provided with a calibration file to make it correspond to a model 4250 instrument. This calibrated model 6250 instrument is used as a pseudomaster for model 4250 field instruments, which are also provided with calibration files to make their outputs virtually the same as the calibrated output from the pseudomaster.

The above description is of preferred embodiments of the invention and many modifications may be made thereto without departing from the spirit and scope of the inventions, which is defined in the appended claims.

What is claimed is:

1. An optical measuring system comprising a master optical instrument comprising means to make optical measurements on test samples at different wavelengths throughout a spectrum, a field optical instrument comprising means to make optical measurements on test samples throughout said spectrum, a computer connected to said field instrument to receive measurement values made by field instrument, said computer comprising means to carry out arithmetic operations on the measurement values received from said field instrument in response to a given test sample to convert said values to a set of calibrated values which are substantially identical to the measurement values that would be obtained from said given test sample by said master instrument, said optical instruments being indexed to make optical measurements in response to different wavelengths at index points incrementally spaced throughout the spectrum, said computer including means to define index locations on said field instrument corresponding to the index points on said master instrument on a one to one basis, said field instrument producing an output for each of said index locations in response to the same wavelength that the master instrument responds to at the corresponding index point, said computer including means storing a plurality of correction coefficients corresponding on a one to one basis to said index locations, said computer further including means to correct the photometric value determined for each of said index locations in accordance with the correction coefficients stored in said computer for the corresponding index location.

2. An optical measuring system as recited in claim 1, wherein said correction coefficients for each of said index locations have predetermined values determined by comparing the measurement values made by said field instrument with the measurement values made by said master instrument on a plurality of samples.

3. An optical measuring system comprising a master optical instrument comprising means to make optical measurements on test samples at different wavelengths throughout a spectrum, a field optical instrument comprising means to make optical measurements on test samples throughout said spectrum, a computer connected to said field instrument to receive measurement values made by field instrument, said computer comprising means to carry out arithmetic operations on the measurement values received from said field instrument in response to a given test sample to convert said values to a set of calibrated values which are substantially identical to the measurement values that would be obtained from said given test sample by said master instrument, said optical instruments being indexed to make said index points incrementally spaced throughout said spectrum, the index points of said field instrument being at different wavelengths than said index points of said master instrument, wherein said computer includes means to define index locations throughout said spectrum in said field instrument corresponding on a one to one basis with said index points in said master instrument, said index locations each being a point on an index scale of said field instrument at which said field instrument will respond to the same wavelength that said master instrument responds to at the corresponding index point on said master instrument.

4. An optical measuring system as recited in claim 3, wherein said computer includes means to derive wave shifted photometric output values for each of said index locations representing the measurement response of said field instrument at said index locations from the measurement values obtained by said field instrument at the index points of said field instrument.

5. An optical measuring system as recited in claim 4, wherein said index locations are determined by comparing the measurement values obtained by said master instrument from a plurality of standard samples with the measurement values obtained by said field instrument from said plurality of said standard samples.

6. A method of calibrating a field optical instrument to correspond to a master optical instrument, wherein said optical instruments are of the type that operate to make optical measurements on test samples at different wavelengths throughout a spectrum, comprising the steps of measuring a plurality of samples with said master instrument to obtain a first file of data comprising measurements on each of said samples at different wavelengths throughout said spectrum, measuring said plurality of samples with said field instrument to obtain a second file of data comprising measurements of each of said samples throughout said spectrum, comparing said first file of data with said second file of data to determine a calibration file of values which when applied to measurement values obtained by said field instrument from an unknown sample will result in corrected values which are substantially identical to the measurement values that would be obtained from said unknown sample by said master instrument, the values in said calibration file each being dependent upon the measurements made by said master instrument upon said plurality of samples and being dependent upon the measurements made by said field instrument upon said plurality of samples, storing said calibration file in a computer and programming said computer to correct the measurements made by said field instrument in accordance with said calibration file.

7. A method as recited in claim 6, wherein said calibration file is determined by statistically correlating said second file of data with said first file of data.

8. A method of calibrating as recited in claim 6, wherein said calibration file includes an identification of a plurality of index locations distributed throughout said spectrum on an index scale of said field instrument, each corresponding on a one to one basis with index points distributed throughout said spectrum on an index scale of said master instrument, said index locations each corresponding to the point on the index scale of said field instrument at which said field instrument will respond to the same wavelength that said master instrument responds to at the corresponding index point.

9. A method of calibration as recited in claim 8, wherein each of said index locations are determined by calculating a point of maximum statistical correlation between the data in said second file and the data in said first file measured at each of said index points of said master instrument.

10. A method of calibration as recited in claim 8, wherein said calibration file includes correction coefficients corresponding on a one to one basis to said index locations and wherein said step of programming said computer includes programming said computer to determine from the measurements made on said unknown sample, a photometric value corresponding to each of said index locations and correcting said photometric values in accordance with the corresponding correction coefficients.

11. An optical measuring system comprising a master optical instrument comprising means to make optical measurements on test samples at different wavelengths throughout a spectrum, a field optical instrument comprising means to make optical measurements on test samples throughout said spectrum, a computer connected to said field instrument to receive measurement values made by field instrument, said computer comprising means to carry out arithmetic operations on the measurement values received from said field instrument in respoinse to a given test sample to convert said values to a set of calibrated values which are substantially identical to the measurement values that would be obtained from said given test sample by said master instrument, said computer including a file of calibration data including values determined by comparing the response of said master instrument to a plurality of samples with the response of said field instrument to said plurality of samples, the values in said calibration file each being independent upon the measurements made by said master instrument upon said plurality of samples and being dependent upon the measurements made by said field instrument upon said plurality of samples, said means to carry out arithmetic operations employing said file of calibration data in said arithmetic operations.

* * * * *